United States Patent [19]
Belofsky et al.

[11] Patent Number: 5,492,902
[45] Date of Patent: Feb. 20, 1996

[54] **INDOLE ANTIINSECTAN METABOLITES FROM THE ASCOSTROMATA OF *EUPENICILLIUM SHEARII***

[75] Inventors: Gilbert N. Belofsky; James B. Gloer, both of Iowa City, Iowa; Donald T. Wicklow; Patrick F. Dowd, both of Peoria, Ill.

[73] Assignees: The United States of America as represented by the Secretary of Agriculture, Washington, D.C.; University of Iowa Research Foundation; Biotechnology Research & Development Corporation, Peoria, Ill.

[21] Appl. No.: 348,571

[22] Filed: Dec. 2, 1994

[51] Int. Cl.$^6$ .................. A01N 43/90; C07D 491/18; C07D 491/22
[52] U.S. Cl. .................. 514/183; 514/410; 540/461; 548/417
[58] Field of Search .................. 540/461; 548/417; 514/183, 410

[56] References Cited

U.S. PATENT DOCUMENTS

| | | | |
|---|---|---|---|
| 4,973,601 | 11/1990 | Dowd et al. | 514/410 |
| 5,130,326 | 7/1992 | Laakso et al. | 514/410 |
| 5,227,396 | 7/1993 | Laakso et al. | 514/410 |
| 5,300,495 | 4/1994 | Laasko et al. | 514/183 |

OTHER PUBLICATIONS

Cole et al., *J. Agric. Food Chem.* 1977, 25, 1197.
deJesus et al., *J. Chem. Soc. Perkin Trans. I* 1984, 697.
Dorner et al., *J. Agric. Food Chem.* 1984, 32, 1069.
Dowd, P. F., *Entomol. Exp. Appl.* 1988, 47, 69.
Gallagher et al., *Tetradedron Lett.* 1980, 21, 239–242.
Gallagher et al., *Tetrahedron Lett.* 1980, 21, 235.
Gloer et al., *J. Org. Chem.* 1989, 54, 2530.
Gloer et al., *J. Org. Chem.* 1988 53, 5457.
Laakso et al., *J. Org. Chem.* 1992, 57, 2066.
Mantle et al., *Xenobiotica* 1990, 20, 809.
Mantle, P. G.; Weedon, C. M., *Phytochemistry* 1994, 36, 1209.
Nozawa et al., *J. Chem. Soc. Perkin Trans. I* 1988, 2607.
Springer et al., *Tetrahedron Lett.* 1975, 30, 2531.
Staub et al., *Tetrahedron Lett.* 1993, 34, 2569.
Stolk, A. C.; Scott, D. B. *Persoonia*, 1967, 4, 391.
TePaske et al. *J. Nat. Prod.* 1992, 55, 1080.
Wicklow et al., *Trans. Br. Mycol. Soc.* 1988, 91, 433.
Wilkins et al., *J. Agric. Food Chem.* 1992, 40, 1307.
Penn et al., *Phytochemistry* 1993, 32, 1431.
Takagi et al., Jpn. Kokai Tokkyo Koho JP 06/65,246 [94/65,246], *Chem. Abstr.* 1994, 121, 155915t.

*Primary Examiner*—Patricia L. Morris
*Attorney, Agent, or Firm*—Arnold, White & Durkee

[57] ABSTRACT

Shearinines A, B and C, and 21-Isopentenylpaxilline are ascostromatal metabolites of the fungus *Eupenicillium shearii*. These indole alkaloid compounds are effective for controlling Coleopteran and Lepidopteran insects and the fall armyworm, *Spodoptera frugiperda*.

13 Claims, No Drawings

INDOLE ANTIINSECTAN METABOLITES FROM THE ASCOSTROMATA OF *EUPENICILLIUM SHEARII*

FIELD OF THE INVENTION

The present invention is generally related to indole alkaloid compounds. More specifically, these compounds are used as insecticides for control of Lepidoptera and Coleoptera species and specifically for control of the Lepidoptera, *Spodoptera frugiperda*.

BACKGROUND OF THE INVENTION

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as *Aspergillus* have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and arthropods during their period of dormancy in soil, have been shown to contain metabolites that exert adverse physiological effects on insects. Gloer et al. [*J. Org. Chem.* 53:5457 (1988)] and Wicklow et al. [*Trans. Br. Mycol. Soc.* 91:433 (1988)] disclose the isolation of four antiinsectan aflavinine derivatives from the sclerotia of *Aspergillus flavus* for use in controlling the dried-fruit beetle *Carpophilus hemipterus* (Nitidulidae:Coleoptera). TePaske et al. [*J. Org. Chem.* 55:5299 (1990)] disclose a related metabolite, aflavazole, which was isolated from extracts of *A. flavus* sclerotia. Gloer et al. [*J. Org. Chem.* 54:2530 (1989)] describe an insecticidal indole diterpene known as nominine found in the sclerotia of *Aspergillus nomius* for the control of the corn earworm *Helicoverpa zea* (Lepidoptera), formerly *Heliothis zea*. Nominine is also disclosed by Dowd et al. in U.S. Pat. No. 5,017,598 issued May 21, 1991, and entitled "Nominine, an Insecticidal Fungal Metabolite".

The compounds penitrem A-F [de Jesus et al., *J. Chem. Perkin Trans. I*, 1847–1861 (1983)] and aflatrem [Gallagher et al., *Tetrahedron Lett.* 21:239 (1980)] are known tremorgenic mycotoxins which are produced by strains of *Penicillium crustosum* and *Aspergillus flavus*, respectively. Paspalinine, paspalicine and paspaline from *Claviceps paspali* are also known to cause tremors in mice and domestic animals [Gallagher et al., *Tetrahedron Lett.* 21:235 (1980); Springer and Clardy, *Tetrahedron Lett.* 21:231 (1980)]. A mechanism of action for these tremorgens is proposed by Setala et al., *Drug Chem. Toxicol.* 12:237 (1989).

Tremorgenic mycotoxins such as penitrem A, aflatrem and paspaline are described by Dowd et al. as possessing insecticidal activity [U.S. Pat. No. 4,973,601, issued Nov. 27, 1990; *J. Antibiot.* 41:1868 (1988)] Dowd et al. disclose a method of controlling insects such as *H. zea* and *S. frugiperda* by applying a fungal tremorgenic metabolite containing an indole moiety to them.

There remains a continuing need for new insecticides because many agriculturally important insect species have developed a resistance to the most potent insecticides which are currently available. Moreover, environmentally tolerable replacements for these insecticides are lacking. New natural, biodegradable insecticides which are relatively nontoxic to vertebrates and may be produced by fermentation processes are a cost-effective replacement for known insecticides.

SUMMARY OF THE INVENTION

In order to satisfy the need for a cost-effective, natural, biodegradable insecticide, one aspect of the present invention provides substantially pure indole alkaloid compounds which are effective for controlling Lepidopteran and Coleopteran insects and the fall armyworm, *Spodoptera frugiperda*. Such compounds have been isolated from ascostromata of *Eupenicillium shearii* and are designated Shearinines A, B, and C, and 21-Isopentenylpaxilline.

Shearinine A ($C_{37}H_{45}NO_5$) has the structure:

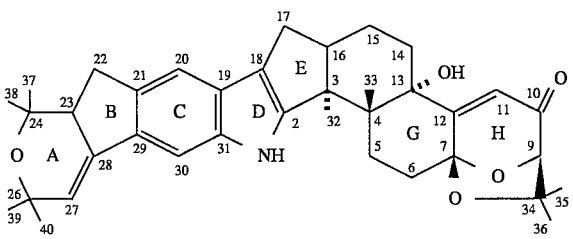

Shearinine B ($C_{37}H_{47}NO_5$) has the structure:

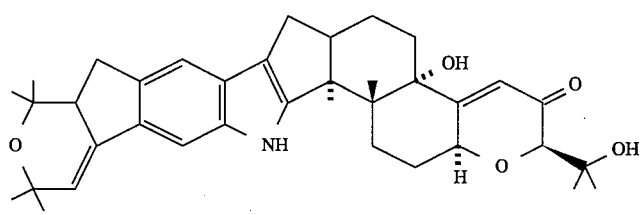

Shearinine C ($C_{37}H_{47}NO_7$) has the structure:

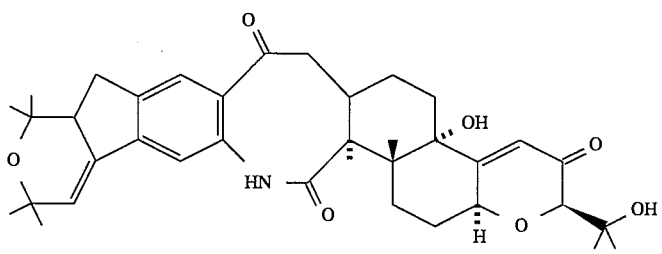

and 21-Isopentenylpaxilline has the structure:

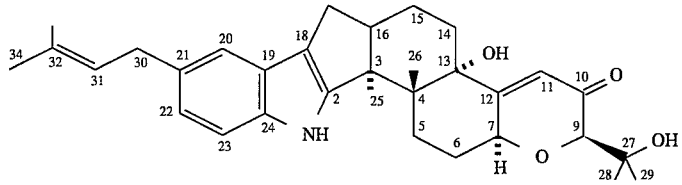

DETAILED DESCRIPTION OF THE INVENTION

The present invention provides several substantially pure indole alkaloid compounds effective in controlling insects, insecticidal compositions containing a compound of the present invention, and a method for controlling insects by applying the compositions to the locus of the insects. The compounds of the present invention have been designated Shearinine A, Shearinine B, Shearinine C, and 21-Isopentenylpaxilline, and are collectively referred to as "the compounds." These compounds were isolated from organic extracts of the sclerotioid ascostromata of *Eupenicillium shearii*.

Antiinsectan metabolites from the sclerotia of ,Aspergillus species have been previously isolated. Gloer et al. [*J. Org. Chem.* 54:2530 (1989)]; Laakso et al. [*J. Org. Chem.* 57:2066 (1992)]; Staub et al. [*P.F. Tetrahedron Lett.* 34:2569 (1993)]. Thus, the investigation of the chemistry of sclerotioid ascostromata of *Eupenicillium shearii* was similarly undertaken. Like sclerotia, ascostromata are hardened physiological structures that provide inoculum upon germination. Chemical investigation of the ascostromata of *Eupenicillium shearii* Stolk and Scott (NRRL 3324) led to the isolation of three new indole alkaloids of the janthitrem class, (see deJesus et al. [*J. Chem. Soc. Perkin Trans.* I 697 (1984)]; Wilkins et al. [*J. Agric. Food Chem.* 40:1307 (1992)]), which are designated Shearinines A, B, and C. An additional new metabolite related to paxilline, a known Penicillium metabolite, Springer et al. [*Tetrahedron Lett.* 30:2531 (1975), was also isolated. That new metabolite is 21-Isopentenylpaxilline. In addition, four known members of the paxilline class, and paxilline itself were also isolated.

The sclerotia of *Eupenicillium shearii* are produced by solid-substrate fermentation on corn kernels. They are ground by conventional means to a suitable particle size and are extracted with at least one solvent. Suitable solvents for the extraction could be readily determined by the skilled artisan and would include any solvents in which the compounds of the present invention are soluble.

Isolation and purification of the compounds of the present invention from the solvent extract is effected by the use of conventional techniques, such as high-performance liquid chromatography (HPLC), thin-layer chromatography (TLC), silica gel column chromatography and countercurrent distribution (CCD). In a preferred embodiment of the invention, a solvent extract is separated by silica gel column chromatography, and the resulting fraction is further separated by reversed-phase HPLC.

Commercial formulations including the compounds of the present invention may be prepared directly from fungal extracts or from the fractions derived from the extracts. However, the formulations are prepared from a pure or a substantially pure compound when a high degree of specificity is required. For example, if a high degree of predictability of the intended response by both target and nontarget species is required, a formulation prepared from a pure or substantially pure form of a compound of the present invention would be used. The formulation would then exclude other substances found in natural fungi which might have an adverse effect on activity or a toxic effect toward nontarget species.

Insecticidal compositions of the present invention include Shearinines A–C and 21-Isopentylpaxilline as described above in combination with a suitable inert carrier as known in the art. Agronomically acceptable carriers such as alcohols, ketones, esters and surfactants are illustrative. A compound of the present invention is present in the composition in an amount effecting the target species which is typically at least about 1.0 ppm. The concentration of the compound in an insecticidal composition will vary considerably depending upon the target species, substrate, method of application and desired response. Addition factors to be considered in determining an optimum concentration include phytotoxicity toward the treated plant and the tolerance of nontarget species.

The compounds of the present invention act to control pests by mechanisms including growth regulation, death inducement, sterilization, as well as interference with metamorphosis and other morphogenic functions. The resulting response is dependent on the pest species, the compound concentration and method of application. The compound is administered in an amount effecting one or more of the responses as may be predetermined by routine testing. Where the intended response is pest mortality, an "effective amount" is defined as the quantity of the compound which will effect a significant mortality rate of a test group as compared with an untreated group. The actual effective amount will vary with the species of pest, stage of larval development, nature of the substrate, the type of inert carrier, the period of treatment and other related factors.

The compositions of the present invention are effective in controlling a variety of insects. Agronomically important insects such as those of the orders Lepidoptera and Coleoptera are of particular interest. In addition, the compositons of the present invention are specifically effective in controlling the Lepidoptera, *Spodoptera frugiperda*. However, the compounds and compositions of the present invention are not limited thereto.

The invention further provides a method of controlling insects by applying the composition to the locus of the pest to be controlled. When the compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest. As shown in Example 4, the antiinsectans of the present invention are up to 94% effective on their target organisms when used at the tested doses.

The following examples are presented to describe preferred embodiments and utilities of the present invention and are not meant to limit the present invention unless otherwise stated in the claims appended hereto.

EXAMPLE 1

Production of Ascostromata of Eupenicillium Shearii

A culture of *E. shearii* Stolk and Scott (NRRL 21130 anamorph state=*Penicillium shearii* Stolk and Scott) was obtained from the Agricultural Research Service (ARS) Collection at the National Center for Agricultural Utilization Research in Peoria, Ill. The ARS collection received this strain in 1968 as CBS 488.66 from the Centraalbureau voor Schimmelcultures, Baarn, The Netherlands. The fungus was originally isolated by J. L. Renard from savannah soil collected near Abidjan, Ivory Coast, and was identified by A. C. Stolk. Stolk et al. [*Persoonia* 4:391 (1967)]. Production of ascostromata was accomplished by solid substrate fermentation on autoclaved corn kernels using procedures described elsewhere. Wicklow et al. [*Trans. Br. Mycol. Soc.* 91:433 (1988)]. The ascostromata were harvested, ground to a powder using a Tecator mill (Perstorp Instrument Co.), and stored at 4° C. until extraction.

EXAMPLE 2

NMR, HMBC, HMQC, HPLC, and DEPT Experimental Protocols $^1$H NMR data was obtained at 300 or 600 MHz on Bruker AC-300 and AMX-600 model spectrometers, respectively, and $^{13}$C NMR data were obtained at 75.5 MHz. HMBC and HMQC data were obtained at 600 MHz ($^1$H dimension), and were optimized for $^nJ_{CH}$=8.3 Hz and $^1J_{CH}$=150.2 Hz, respectively. All spectra were recorded in CDCl$_3$ and chemical shifts were referenced using the corresponding solvent signals at 7.24 ppm or 77.0 ppm. Multiplicities of carbon signals were determined through DEPT experiments, and all carbon assignments are consistent with the DEPT results. Analytical HPLC separations were accomplished using a Rainin Microsorb MV C$_{18}$ column (5 μm particles, 4.6 mm×25 cm) at a flow rate of 1.2 mL/min with UV detection at 254 nm. Preparative HPLC separations were accomplished using a Rainin Dynamax-60A C$_{18}$ column (8 μm particles, 21.4 mm×25 cm) at a flow rate of 10 mL/min with UV detection at 254 nm. EIMS data were recorded at 70 eV using a VG Trio 1 quadrupole mass spectrometer, and HREIMS and FABMS experiments were performed on a VG ZAB-HF mass spectrometer. Thin layer chromatography employed silica gel (Merck Kieselgel 60 F254, 0.25 mm) eluting with 9:1 CH$_2$Cl$_2$-MeOH. Visualization of tlc spots was accomplished by exposure to UV light at 254 nm and to a vanillin/H$_2$SO$_4$ (1% w/v) spray reagent. Details of feeding assays have been described previously. Dowd [*Entomol. Exp. Appl.* 47:69 (1988)].

EXAMPLE 3

Isolation of Insecticidal Compounds

A sample of powdered *E. shearii* ascostromata (39 g) was extracted at room temperature by stirring successively in hexane, CH$_2$Cl$_2$, EtOAc, and MeOH. The combined crude EtOAc and MeOH extracts (1.4 g) were preadsorbed onto 5 g of silica gel in a solution of 2:1 CH$_2$Cl$_2$-MeOH. This mixture was concentrated under vacuum and the resulting powder was subjected to silica gel vacuum liquid chromatography over a prepacked column bed (3.3×4 cm). The column was eluted using a stepwise gradient of MeOH (0–100%) in CH$_2$Cl$_2$, and a total of twelve 100 or 200 mL fractions were collected. The six fractions that eluted with 0% to 15% MeOH were combined (390 mg) and fractionated by gel filtration on Sephadex LH-20 (2×50 cm) with 1:1 CH$_2$Cl$_2$-MeOH. Fractions of similar composition as determined by TLC were pooled. The resulting active fraction (125 mg) was separated further by silica gel chromatography (2×13 cm) using a linear gradient of MeOH (0–10%) in CH$_2$Cl$_2$. Fractions of similar composition as determined by TLC were pooled. The second and third fractions pooled in this manner (11 mg and 10 mg, respectively) contained mixtures of less polar compounds with R$_f$ values between 0.5 and 0.9 by TLC. These two fractions were further purified by preparative reversed-phase HPLC (CH$_3$CN-H$_2$O) to afford Shearinine A (3.3 mg), Shearinine B (3.5 mg), and 21-Isopentenylpaxilline (4.1 mg).

The CH$_2$Cl$_2$ extract of the same 39 g ascostromatal sample (272 mg) was fractionated by gel filtration on Sephadex LH-20 (2×50 cm) with 3:1:1 hexane-toluene-MeOH. Fractions of similar composition as determined by TLC were combined. The resulting active fraction (28 mg) was further purified by preparative reversed-phase HPLC to yield additional amounts of compounds Shearinine A (6.4 mg), Shearinine B (6.6 mg), and 21-Isopentenylpaxilline (3.4 rag).

A second powdered ascostromatal sample (320 g) was extracted by stirring successively in hexane, CH$_2$Cl$_2$, EtOAc, and MeOH. The combined crude CH$_2$Cl$_2$, EtOAc, and MeOH extracts (13.4 g) were subjected to fractionation procedures similar to those described above. Gel filtration on Sephadex LH-20 (3:1:1 hexane-toluene-MeOH) yielded 7-Hydroxy-13-dehydroxypaxilline (11.6 mg) and Paspalinine (26.5 mg). After gel filtration and silica gel chromatography, other fractions of similar composition as determined by TLC were subjected to preparative reversed-phase HPLC ($CH_3CN$—$H_2O$ and MeOH—$H_2O$) to yield Shearinine C (18.1 mg), Paxilline (65.1 mg), 13—Dehydroxypaxilline (14.0 mg), 2,18-Dioxo-2,18-secopaxilline (8.7 rag), as well as additional amounts of Shearinine A (40.3 mg) and Shearinine B (48.5 mg).

EXAMPLE 4

Chemical Data on Antiinsecticidal Compounds

After the antiinsecticidal compounds of the present invention were isolated by bioassay-guided fractionation of organic extracts of ascostromata produced by solid-substrate fermentation of *E. shearii* NRRL 21130, the compounds were analyzed to determine their structures and antiinsecticidal activities.

Fractions from chromatography on silica gel and reversed-phase HPLC were tested in feeding assays against larvae of *Helicoverpa zea* (corn earworm) and *Carpophilus hemipterus* (driedfruit beetle) in order to isolate constituents with antiinsectan activity. Shearinine A has the molecular formula $C_{37}H_{45}NO_5$, as deduced from mass spectral data (EIMS $M^+$ at m/z 583; HREIMS M- $CH_3$ at m/z 568.3063, $\Delta$–2.9 mmu). The $^1H$ NMR spectrum contained eight aliphatic methyl singlets, two aromatic proton singlets, and an N-H singlet. DEPT, HMBC, and HMQC experiments permitted the corresponding proton and carbon assignments to be made. The NMR data, particularly the number of methyl singlets, suggested that Shearinine A is a representative of the janthitrem class.

Detailed comparison of the data for Shearinine A with those of the known compound Janthitrem E supported this conclusion, but also revealed several significant differences from the known members of this class. First, the hydroxyl group at C-10 in Janthitrem E is replaced by a ketone in Shearinine A, for which a carbon signal appears at 197.0 ppm. The hydroxyl group at C-22 in Janthitrem E is absent in compound Shearinine A, as evidenced by the lack of a corresponding proton signal at 4.90 ppm, and the presence of two new methylene proton signals at 3.10 and 2.66 ppm. This was further confirmed by long range correlations of $H_2$-22 with the neighboring indole aryl carbons and with C-23 and C-28 of the five-membered B-ring. Finally, C-7 of Shearinine A is not protonated, and is relatively deshielded (104.4 ppm) when compared to the corresponding signal of Janthitrem E. These features indicated the presence of an additional ring (the I-ring) in Shearinine A, and accounted for the difference in elemental composition between Shearinine A and Janthitrem E. The remaining $^1H$ and $^{13}C$ NMR assignments were very similar to those of Janthitrem E. The gross structure of Shearinine A was therefore assigned as Shearinine A, with relative stereochemistry proposed on the basis of $^1H$ NMR J-values, NOESY data, and structural analogy to Janithitrem E.

The $^1H$ NMR spectrum of Shearinine B ($C_{37}H_{47}NO_5$) was nearly identical to that of Shearinine A except for the presence of an additional exchangeable OH signal at 4.10 ppm (C-34-OH) and an additional doublet of doublets at 4.83 ppm, corresponding to H-7. These changes suggested that compound Shearinine B lacks a closed I-ring. Furthermore, the C-7 carbon signal appears as a doublet at 72.6 ppm (as opposed to a singlet at 104.4 ppm in Shearinine A), and C-9 is shifted upfield to 83.3 ppm (from 87.9 ppm in Shearinine A). These data are consistent with those observed for 21-Isopentenylpaxilline, Paxilline, Janthitrem E, and related metabolites with the analogous structural subunit. Cole et al. [*J. Agric. Food Chem.* 25:1197 (1977)]; Dorner et al. [*J. Agric. Food Chem.* 32:1069 (1984). These results led to the assignment of the structure of Shearinine B as Shearinine B.

Shearinine C was shown by $^{13}C$ NMR and LRFABMS to have the molecular formula $C_{37}H_{47}NO_7$. Carbon signals at 203.9 ppm and at 176.2 ppm suggested the presence of two carbonyl carbons not present in Shearinine B, accounting for the additional oxygen atoms in the molecular formula of Shearinine C. Many of the carbon signals of Shearinine C were similar to those of Shearinine B, but the pattern of $^{13}C$ signals associated with the C-15 through C-21 portion of the molecule suggested an alteration in the indole subunit. Comparison of the $^1H$ and $^{13}C$ NMR data for Shearinine C with those for the known compounds 2,18-dioxo-2,18-secopaxilline), Mantle et al. [*Xenobiotica* 20:809 (1990)], and sulpinine C, Laakso et al. [*J. Org. Chem.* 57:2066 1992), indicated the presence of an eight-membered ketoamide central ring in Shearinine C, presumably formed via oxidation of the indole C2-C-3 bond of Shearinine B. This was further confirmed by the FAB mass spectrum of Shearinine C which showed a characteristic ion at m/z 270 ($C_{17}H_{19}NO_2$+H) resulting from cleavage through the eight-membered ring between C-17 and C-18, and through the amide bond, as was reported for compound 2,18-Dioxo-2, 18-seco-paxilline. Mantle et al. [*Xenobiotica* 20:809 (1990). The complete $^1H$ and $^{13}C$ NMR assignments for Shearinine C were determined by analysis of HMBC, HMQC, and COSY experiments.

A new paxilline analog was also obtained from the organic extracts of *E. shearii* ascostromata. A molecular formula of $C_{32}H_{41}NO_4$ for this metabolite (21-Isopentenyl-paxilline) was deduced from $^{13}C$ NMR and LRFABMS data. Examination of the NMR data indicated that 21-Isopentenylpaxilline is similar in structure to the known indole alkaloids paxilline and paspalinine. Comparison of the $^{13}C$ NMR spectrum of 21-Isopentenylpaxilline) with the spectrum for an authentic sample of Paxilline revealed that compound 21-Isopentenylpaxilline) differs from Paxilline by the addition of an isopentenyl group at C-21. The $^1H$ and $^{13}C$ NMR assignments for 21-Isopentenylpaxilline) (see Experimental), as well as the location of the isopentenyl unit, were determined by analysis of HMBC and HMQC data.

Five related known compounds, 7-hydroxy-13-dehydroxypaxilline, paxilline, 13-dehydropaxilline, 2,18-dioxo-2,18-seco-paxilline, and paspalinine were also isolated from *E. shearii* ascostromata. Identification of these compounds was accomplished by analysis of LRFABMS, NMR, COSY, and/or HMBC experiments, and by comparison with authentic standards and literature values. Springer et al. [*Tetrahedron Lett.* 30:2531 (1975)]; Mantle et al. [*Xenobiotica* 20:809 (1990)]; Nozawa et al. [*J. Chem. Soc. Perkin Trans. I* 2607 (1988)]; Gallagher et al. [*Tetrahedron Lett.* 21:235 (1980); Mantle et al. [*Phytochemistry* 36:1209 (1994)].

Interestingly, all of the compounds containing intact indole subunits (Shearinine A, Shearinine B, 21-Isopentenylpaxilline, 7-Hydroxy-13-dehydroxypaxilline, Paxilline, 13-Dehydroxypaxilline, and Paspalinine) gave FAB mass spectra wherein the $M^+$ion was significantly more intense than the expected $(M +H)^+$ion. This was found to be the case in several different FAB matrices, including glycerol, thioglycerol, 1:1 dithioerythritol-dithiothreitol, and 3-nitrobenzyl alcohol.

Tables 1–3 describe NMR Spectral Data for Shearinines A–C.

TABLE 1

NMR Spectral Data for Shearinine A

| position | ¹H | ¹³C | HMBC correlations |
|---|---|---|---|
| 1 | 7.63 (s) | — | 2, 18, 19, 31 |
| 2 | — | 153.2 | |
| 3 | — | 51.6 | |
| 4 | — | 39.9 | |
| 5 | 2.66 (m) | 27.0 | 3, 6, 7, 33 |
|   | 1.80 (m) |      | 13, 33 |
| 6 | 2.77 (m) | 28.2 | 5, 7 |
|   | 2.04 (m) |      | 4, 5, 7, 12 |
| 7 | — | 104.4 | |
| 9 | 4.29 (d; 1) | 88.0 | 7, 10, 11, 36 |
| 10 | — | 197.0 | |
| 11 | 5.81 (d; 1) | 117.7 | 7, 9, 12, 13 |
| 12 | — | 169.8 | |
| 13 | — | 77.7 | |
| 14 | 1.97 (ddd; 13.1, 13.0, 4.2) | 33.9 | |
|    | 1.88 (br d; 13.6) | | |
| 15 | 2.04 (m) | 21.1 | |
|    | 1.80 (m) |      | 13 |
| 16 | 2.77 (m) | 48.5 | |
| 17 | 2.66 (m) | 27.5 | 2, 3, 16, 18 |
|    | 2.40 (dd; 13.0, 10.7) | | 2, 18 |
| 18 | — | 117.0 | |
| 19 | — | 127.0 | |
| 20 | 7.24 (s) | 114.0 | 18, 19, 22, 29, 31 |
| 21 | — | 137.0 | |
| 22 | 3.10 (dd; 15.7, 9.3) | 33.0 | 20, 21, 23, 28, 29 |
|    | 2.66 (m) | | 21, 24, 23 |
| 23 | 2.92 (m) | 48.8 | 24, 28 |
| 24 | — | 74.5 | |
| 26 | — | 72.6 | |
| 27 | 5.91 (d; 3.0) | 119.9 | 23, 26, 29 |
| 28 | — | 139.5 | |
| 29 | — | 133.5 | |
| 30 | 7.32 (s) | 102.9 | 19, 20, 21, 28 |
| 31 | — | 139.9 | |
| 32 | 1.38 (s) | 16.2 | 2, 3, 4, 16 |
| 33 | 1.21 (s) | 23.6 | 3, 4, 5, 13 |
| 34 | — | 78.8 | |
| 35 | 1.17 (s) | 23.08 | 9, 34, 36 |
| 36 | 1.43 (s) | 28.9 | 9, 34, 35 |
| 37 | 1.32 (s) | 30.0 | 23, 24, 38 |
| 38 | 1.07 (s) | 22.0 | 23, 24, 37 |
| 39 | 1.32 (s) | 31.9 | 26, 27, 40 |
| 40 | 1.34 (s) | 30.1 | 26, 27, 39 |

TABLE 2

NMR Spectral Data for Shearinine B

| position | ¹H | ¹³C | HMBC correlations |
|---|---|---|---|
| 1 | 7.71 (s) | — | 2, 18, 19, 31 |
| 2 | — | 152.9 | |
| 3 | — | 50.9 | |
| 4 | — | 43.2 | |
| 5 | 2.77 (m) | 27.2 | 3, 6, 33 |
|   | 1.44 (dd; 13.2, 4.7) | | 4, 6, 7, 13, 33 |
| 6 | 2.31 (m) | 28.5 | 4, 5, 7, 12 |
|   | 1.88 (m) |      | 5, 7 |
| 7 | 4.83 (br dd; 9.8, 8.3) | 72.6 | 6, 11, 12 |
| 9 | 3.68 (d; 1.9) | 83.3 | 7, 35, 36 |
| 10 | — | 199.2 | |
| 11 | 5.83 (d; 1.8) | 119.7 | 7, 9, 13 |
| 12 | — | 168.1 | |
| 13 | — | 77.2 | |
| 14 | 2.00 (m) | 34.3 | 15, 16 |
|    | 1.59 (m) |      | 4, 13, 16 |
| 15 | 2.00 (m) | 20.9 | 14 |
|    | 1.75 (m) |      | 3, 13 |
| 16 | 2.77 (m) | 49.4 | 4 |
| 17 | 2.67 (m) | 28.0 | 2, 3, 16, 18 |
|    | 2.40 (dd; 13.0, 11.0) | | 2, 15, 16, 18 |
| 18 | — | 117.3 | |
| 19 | — | 126.4 | |
| 20 | 7.25 (s) | 114.1 | 18, 19, 22, 29, 31 |
| 21 | — | 137.0 | |
| 22 | 3.10 (dd; 15.6, 9.4) | 33.0 | 20, 21, 23, 28, 29 |
|    | 2.67 (m) | | 21, 23, 24 |
| 23 | 2.91 (m) | 48.8 | 22, 24, 27, 28, 37, 38 |
| 24 | — | 74.5 | |
| 26 | — | 72.5 | |
| 27 | 5.90 (d; 3.0) | 120.0 | 23, 26, 29, 40 |
| 28 | — | 139.5 | |
| 29 | — | 133.7 | |
| 30 | 7.33 (s) | 102.9 | 19, 21, 28 |
| 31 | — | 139.7 | |
| 32 | 1.31 (s) | 16.1 | 2, 3, 4 |
| 33 | 0.98 (s) | 19.7 | 3, 4, 5, 13 |
| 34 | — | 72.6 | |
| 35 | 1.26 (s) | 24.2 | 9, 34, 36 |
| 36 | 1.28 (s) | 26.6 | 9, 34, 35 |
| 37 | 1.32 (s) | 30.0 | 24, 38 |
| 38 | 1.07 (s) | 22.0 | 23, 24, 37 |
| 39 | 1.32 (s) | 31.9 | 26, 27, 40 |
| 40 | 1.34 (s) | 30.1 | 26, 27, 39 |

TABLE 3

NMR Spectral Data for Shearinine C

| position | ¹H | ¹³C | HMBC correlations |
|---|---|---|---|
| 1 | 7.09 (s) | — | 2, 3, 19, 30 |
| 2 | — | 176.2 | |
| 3 | — | 57.2 | |
| 4 | — | 44.0 | |
| 5 | 2.50 (ddd; 14.1, 14.1, 4.4) | 25.1 | 4, 6, 13, 33 |
|   | 1.90 (m) | | 4, 6, 7, 13 |
| 6 | 2.18 (m) | 28.2 | 4, 7 |
|   | 1.66 (m) |      | 5, 7 |
| 7 | 4.71 (dd; 10.2, 8.2) | 72.6 | 6, 11, 12 |
| 9 | 3.59 (d; 2.1) | 83.0 | 34, 35, 36 |
| 10 | — | 199.2 | |
| 11 | 5.70 (d; 1.9) | 120.1 | 7, 9, 13 |
| 12 | — | 168.2 | |
| 13 | — | 76.6 | |
| 14 | 1.90 (m) | 32.0 | 4, 15 |
|    | 1.48 (m) |      | 4, 13 |
| 15 | 1.74 (m) | 25.2 | 13, 16 |
|    | 1.48 (m) |      | 16 |
| 16 | 3.04 (m) | 35.5 | 3, 18 |
| 17 | 3.04 (m) | 47.7 | 3, 15, 16, 18 |
|    | 2.42 (dd; 17.8, 3.2) | | 3, 15, 16, 18 |
| 18 | — | 203.0 | |
| 19 | — | 134.2 | |
| 20 | 7.49 (s) | 125.9 | 18, 22, 29, 31 |
| 21 | — | 144.2 | |
| 22 | 3.04 (m) | 33.1 | 21, 23, 27, 28, 29 |
|    | 2.61 (dd; 16.3, 8.0) | | 21, 23, 24, 29 |
| 23 | 2.87 (ddd; 8.6, 8.6, 3.0) | 48.5 | 22, 24, 27, 28, 37, 38 |
| 24 | — | 74.2 | |
| 26 | — | 72.6 | |
| 27 | 6.03 (d; 3.1) | 126.3 | 23, 26, 29 |
| 28 | — | 137.5 | |
| 29 | — | 144.6 | |
| 30 | 7.00 (s) | 118.5 | 19, 21, 28, 31 |
| 31 | — | 136.0 | |
| 32 | 1.59 (s) | 16.5 | 2, 3, 4, 16 |
| 33 | 0.95 (s) | 19.9 | 3, 4, 5, 13 |
| 34 | — | 72.6 | |
| 35 | 1.18 (s) | 24.0 | 9, 34, 36 |
| 36 | 1.23 (s) | 26.5 | 9, 34, 35 |
| 37 | 1.31 (s) | 29.9 | 23, 24, 38 |
| 38 | 1.10 (s) | 22.3 | 23, 24, 37 |

TABLE 3-continued

NMR Spectral Data for Shearinine C

| position | $^1$H | $^{13}$C | HMBC correlations |
|---|---|---|---|
| 39 | 1.28 (s) | 31.4 | 26, 27, 40 |
| 40 | 1.34 (s) | 29.7 | 26, 27, 39 |

EXAMPLE 5

Antiinsecticidal Activity

The isolated yields of all nine compounds obtained from the *E. shearii* ascostromata were limited by the complexity of the mixtures, but TLC and HPLC analysis indicated that Shearinines A and B are major components of the ascostromatal extracts. As summarized in Table 4, most of the compounds showed significant antiinsectan activity. For example, incorporation of Shearinine A into a standard pinto bean test diet caused an 89% reduction in weight gain of *H. zea* larvae relative to controls at a dietary concentration of 100 ppm. The same concentration caused a 69% reduction in feeding rate by the fungivorous larvae *C. hemipterus*. The ring-opened analogs Shearinine C and 2,18-Dioxo-2,18-seco-paxilline were significantly less active than their indole-containing counterparts in both assays, and the only compound lacking an OH group at C-13 (13-Dehydroxy-paxilline) was essentially inactive at 100 ppm. Shearinine A also showed activity in a topical assay against first instar larvae of *H. zea*, causing an 80% reduction in weight gain relative to controls when applied to the dorsa at 2 μg/insect. Shearinine B and Paxilline were also tested for activity in a leaf disk assay against the fall armyworm *Spodoptera frugiperda*. Addition of 50 μg of either compound to a 75-mg cotton leaf disk fed to *S. frugiperda* larvae resulted in 84% mortality and 85% reduction in leaf damage relative to controls. The commercial insecticide malathion gives similar results, albeit at one-tenth of this level.

Several compounds related to shearinines A–C, the janthitrems, were previously reported from liquid cultures of *Penicillium janthinellum*, an organism associated with toxic ryegrass pastures. deJesus [*J. Chem. Soc. Perkin Trans. I* 697 (1984)]; Wilkins et al. [*J. Agric. Food Chem.* 40:1307 (1992). None of the known janthitrems were isolated from *E. shearii* ascostromata in the present investigation. The occurrence of novel antiinsectan metabolites in Eupenicillium ascostromata is analogous to the discovery of a considerable number of new antiinsectan compounds we have reported from sclerotia of Aspergillus spp. Gloer et al. [*J. Org. Chem.* 54:2530 (1989)]; Laakso et al. [*J. Org. Chem.* 57:2066 (1992)]; Staub et al. [*Tetrahedron Lett.* 34:2569 (1993)]. These results suggest that fungal ascostromata may be an equally promising source of new bioactive natural products.

Table 4 demonstrates antiinsectan activity of Shearinines A–C, 21-Isopentenylpaxilline, and related compounds from *E. Shearii*.

TABLE 4

Antiinsectan Activity of Shearinines A–C and Related Compounds from *E. Shearii*.[a]

| Compound | *H. zea* larvae (% RGR) | *C. hemipterus* larvae (% RFR) |
|---|---|---|
| Shearinine A | 89 | 69[b] |
| Shearinine B | 94 | 50 |
| Shearinine C | 33 | 19 |
| 21-Isopentenylpaxilline | 55 | 12.5 |
| 7-Hydroxy-13-dehydroxy-paxilline | 83 | 38 |
| Paxilline | 65 | 38 |
| 13-Dehydroxypaxilline | 0 | 12 |
| 2,18-Dioxo-2,18-seco-paxilline | 17 | 19 |
| Paspalinine | 75 | 62 |

[a]Results were obtained upon feeding standard test diets containing 100 ppm of the compound to be tested. Values given are % RGR (% reduction in growth rate relative to controls) and % RFR (% reduction in feeding rate relative to controls). NT = not tested.
[b]Shearinine A also caused a 48% RGR against *C. hemipterus* adults in this assay.

EXAMPLE 6

Analytical Data For Compounds Isolated From *Eupenicillium shearii*

Shearinine A: white solid; $[\alpha]_D$+16.0° (c=0.002 g/mL, CHCl$_3$); analytical HPLC $t_R$ 17.16 min (80:20 CH$_3$CN:H$_2$O); UV (MeOH) 255 (ε25930), 330 nm (20040); IR 3581, 3474, 3020, 2976, 2934, 2857, 1689, 1455, 1365 cm$^{-1}$; $^1$H NMR and $^{13}$C NMR data see Table I; FABMS (3-NBA) m/z 583 (M$^+$, rel. int. 78), 568 (100), 526 (18), 510 (25); EIMS (70 eV) m/z 583 (M$^+$, rel. int. 28), 568 (100), 553 (2.6), 526 (34), 511 (53), 452 (23); HREIMS obsd. 568.3034 (M-CH$_3$), calc. for C$_{37}$H$_{45}$NO$_5$ -CH$_3$, 568.3063; HRFABMS (3-NBA), obsd. 583.3250 (M$^+$), calcd. for C$_{37}$H$_{45}$NO$_5$, 568.3298.

Shearinine B: white solid; $[\alpha]_D$–75.5° (c=0.002 g/mL, CHCl$_3$) analytical HPLC $t_R$ 16.03 min (80:20 CH$_3$CN:H$_2$O); UV (MeOH) 257 (ε26190), 334 nm (20320); IR 3477, 2976, 2929, 2853, 1663, 1460, 1357 cm$^{-1}$; $^1$H NMR and $^{13}$C NMR data, see Table II; FABMS (3-NBA) m/z 585 (M$^+$, rel. int. 27), 570 (79) 526 (8.7), 512 (18), 482 (12), 454 (6.0), 436 (4.9); EIMS (70 eV) m/z 527 (M-C$_3$H$_6$O, rel. int. 5.3), 512 (31), 494 (19), 454 (4.1), 436 (5.1); HRFABMS (thioglycerol), obsd. 585.3425 (M$^+$), calcd. for C$_{37}$H$_{47}$NO$_5$, 568.3454.

Shearinine C: yellow solid; $[\alpha]_D$–146.5° (c=0.002 g/mL, CHCl$_3$); analytical HPLC $t_R$ 4.33 min (80:20 CH$_3$CN:H$_2$O); UV (MeOH) 246 (ε23290), 299 nm (9590); $^1$H NMR and $^{13}$C NMR data see Table III; FABMS (3-NBA) m/z 618 [(M +H)$^+$; rel. int. 100], 602 (51), 582 (9), 558 (17), 542 (27), 531 (8.6), 490 (7.5), 339 (13); HRFABMS (glycerol), obsd. 618.3425 (M+H)$^+$, calcd. for C$_{37}$H$_{47}$NO$_7$+H, 618.3431.

21-Isopentenylpaxilline: white solid; analytical HPLC $t_R$ 35.38 min (80:20 CH$_3$CN:H$_2$O); UV (MeOH) 236 (ε19540), 283 nm (4880); $^1$H NMR (CDCl$_3$) H-1, 7.63 (s); H-5, 2.75 (ddd; 13.8, 13.8, 5.0), 1.45 (m); H$_2$-6, 2.30 (m), 1.83 (m); H-7, 4.84 (dd; 10.0, 8.2); H-9, 3.71 (d;1.8); H-11, 5.87 (d; 2.0); H$_2$-14, 2.05 (m), 1.64 (br d;12.0); H$_2$-15, 2.03 (m), 1.77 (m); H-16, 2.82 (m); H$_2$-17, 2.70 (dd;13.2, 6.3), 2.42 (dd; 13.2, 10.9); H-20, 7.21 (br s); H-22, 6.90 (dd; 8.3, 1.6); H-23, 7.18 (d; 8.3); H$_3$-25, 1.30 (s); H$_3$-26, 1.01 (s); H$_3$-28, 1.26 (s); H$_3$-29, 1.28 (s); H$_3$-30 3.38 (d; 7.3), 1.72 (d; 8.1); H-31, 5.35 (br t; 7.3); H$_3$-33, 1.71 (s); H$_3$-34, 1.70 (s); $^{13}$C NMR (CDCl$_3$) C-2, 151.8; C-3, 50.1; C-4, 43.2; C-5, 28.0; C-6, 28.5; C-7, 72.6; C-9, 83.3; C-10, 199.2; C-11,119.6; C-12, 168.1; C-13, 77.0; C-14, 34.4; C-15,209; C-16, 49.4; C-17, 27.2; C-18, 117.2; C-19, 124.6; C-20, 117.7; C-21, 133.3; C-22, 121.5; C-23,111.3; C-24, 138.3; C-25, 16.2; C-26, 19.8; C-27, 72.4; C-28, 24.2; C-29, 26.6; C-30, 34.5; C-31,124.6; C-32, 131.3; C-33, 17.8; C-34, 25.8; FABMS (3-NBA) m/z 503 (M$^+$, rel. int. 8.6), 488 (7.2), 358 (5.4), 356 (8,8), 330 (6.5).
EXAMPLE 7
Structures of Compounds Isolated from *Eupenicillium shearii*
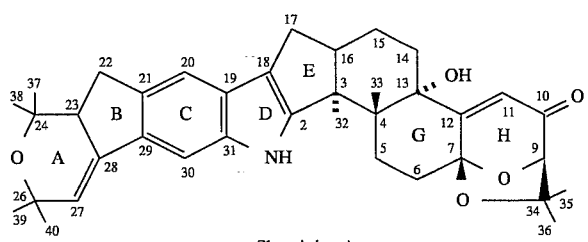
Shearinine A
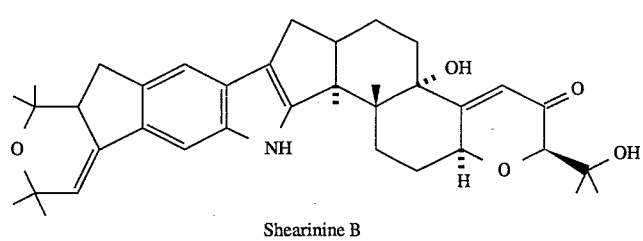
Shearinine B
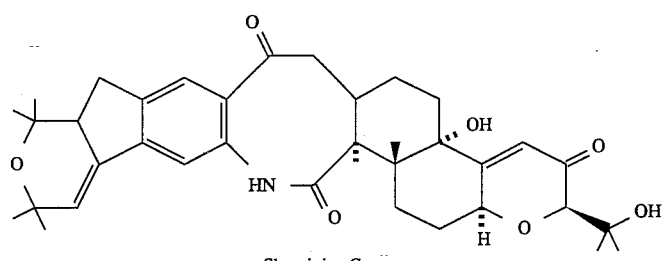
Shearinine C
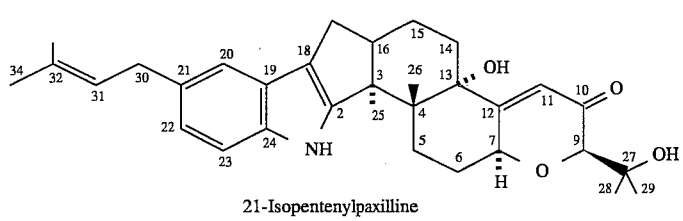
21-Isopentenylpaxilline
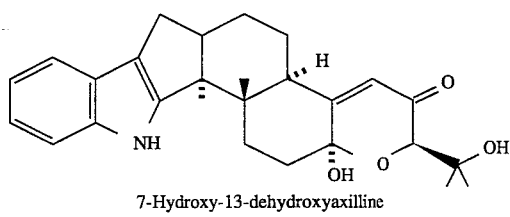
7-Hydroxy-13-dehydroxyaxilline
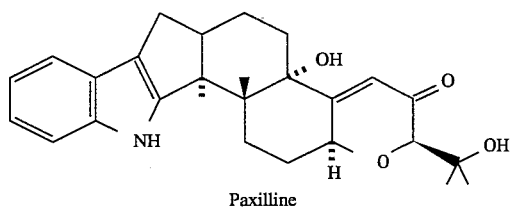
Paxilline

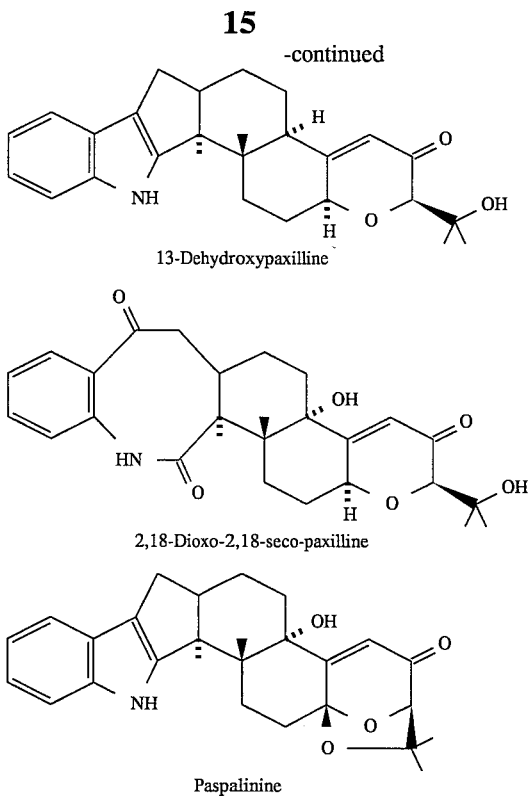

13-Dehydroxypaxilline 2,18-Dioxo-2,18-seco-paxilline

Paspalinine

In addition to using Shearinines A–C and 21-Isopentenylpaxilline as anti-insectants, it is believed that analogs of these molecules will show biological activity. Thus, optimization of the biological activity of these complex natural anti-insectants through the creation of analogs is currently underway.

Two strategies are used to optimize the biological activity of Shearinines A–C and 21-Isopentenylpaxilline. First, since the molecules can be easily prepared from fermentation, semisynthesis involving specific chemical transformations on the functional group handles provided by the natural product is being performed. Second, the preparation of pieces or fragments of Shearinines A–C and 21-Isopentenylpaxilline is being undertaken in order to identify fragments of the original molecules which possess biological activity comparable to, or superior to, the natural product.

Illustrative examples of the above described analog synthesis strategies follow using Shearine B as a model. Under no circumstances, however, should the examples presented be construed to be exhaustive or complete.

EXAMPLE 8

Semisynthesis of Analogs Utilizing Shearinine B as Substrate

Examples of semisynthesis from the natural product.

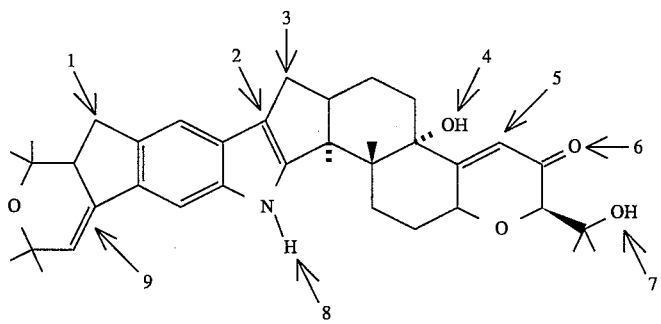

1,3. benzylic oxidation/halogenation 2. reduction, functionalization at C-3 of indole nucleus 5,9. reduction, epoxidation 8. acylation/alkylation 4,7. acylation, alkylation, elimination, oxidation, halogenation 6. reduction; conversion to oxime, hydrazone

EXAMPLE 9

Fragment Synthesis—Biological Activity in Smaller Fragments of Shearine B

Literature Cited:

Cole, R. J.; Dorner, J. W.; Lansden, J. A.; Cox, R. H.; Papa, C.; Cunfer, B. M.; Nicholson, S. S.; Bedell, D. M. *J. Agric. Food Chem.* 1977, 25, 1197.

deJesus, A. E.; Steyn, P. S.; vanHeerden, F. R.; Vleggaar, R. *J. Chem. Soc. Perkin Trans.* I 1984, 697.

Dorner, J. W.; Cole, R. J.; Cox, R. H.; Cunfer, B. M. *J. Agric. Food Chem.* 1984, 32, 1069.

Dowd, P. F. *Entomol. Exp. Appl.* 1988, 47, 69.

Gallagher, R. T.; Finer, J.; Clardy, J.; Leutwiler, A.; Weibel, F.; Acklin, W.; Arigoni, D. *Tetrahedron Lett.* 1980, 21,235.

Gloer, J. B.; Rinderknecht, B. L.; Wicklow, D. T.; Dowd, P. F. *J. Org. Chem.* 1989, 54, 2530.

Laakso, J. A.; Gloer, J. B.; Wicklow, D. T.; Dowd, P. F. *J. Org. Chem.* 1992, 57, 2066.

Mantle, P. G.; Burt, S. J.; MacGeorge, K. M.; Bilton, J. N.; Sheppard, R. N. *Xenobiotica* 1990, 20, 809.

Mantle, P. G.; Weedon, C. M. *Phytochemistry* 1994, 36, 1209.

Nozawa, K.; Nakajima, S.; Kawai, K.; Udagawa, S. *J. Chem. Soc. Perkin Trans.* 1 1988, 2607.

Springer, J. P.; Clardy, J.; Wells, J. M.; Cole, R. J.; Kirksey, J. W. *Tetrahedron Lett.* 1975, 30, 2531.

Staub, G. M.; Gloer, K. B.; Gloer, J. B.; Wicklow, D. T.; Dowd, P. F. *Tetrahedron Lett.* 1993, 34, 2569.

Stolk, A. C.; Scott, D. B. *Persoonia*, 1967, 4, 391.

Wicklow, D. T.; Dowd, P. F.; TePaske, M. R.; Gloer, J. B. *Trans. Br. Mycol. Soc.* 1988, 91,433.

Wilkins, A. L.; Miles, C. O.; Ede, R. M.; Gallagher, R. T.; Munday, S. C. *J. Agric. Food Chem.* 1992, 40, 1307.

We claim:

1. A substantially pure indole alkaloid selected from the group consisting of Shearinine A having the formula ($C_{37}H_{45}NO_5$) and the structure:

Shearinine B having the formula ($C_{37}H_{47}NO_5$) and the structure:

Shearinine C having the formula ($C_{37}H_{47}NO_7$) and the structure:

21-Isopentenylpaxilline having the formula and the structure:

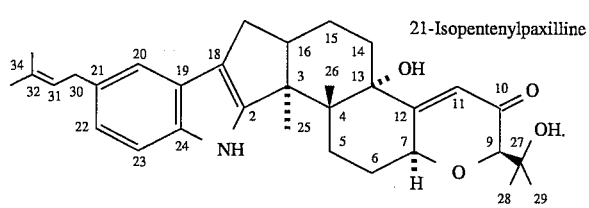

21-Isopentenylpaxilline

2. A composition for controlling insects comprising: an insecticide selected from the group consisting of Shearinine A, Shearinine B, Shearinine C, and 21-Isopentenylpaxilline; and an inert carrier.

3. The composition of claim 2 including an amount of the insecticide affecting insects of the order Coleoptera.

4. The composition of claim 2 including an amount of the insecticide affecting *Carpophilus hemipterus*.

5. The composition of claim 2 including an amount of the insecticide affecting insects of the order Lepidoptera.

6. The composition of claim 2 including an amount of the insecticide affecting *Helicoverpa zea*.

7. The composition of claim 2 including an amount of the insecticide affecting *Spodoptera frugiperda*.

8. A method of controlling insects comprising applying an effective amount of an insecticide selected from the group consisting of Shearinine A, Shearinine B, Shearinine C, and 21-Isopentenylpaxilline to a locus of insects.

9. The method of claim 8 wherein the insects are Coleopteran species.

10. The method of claim 8 wherein the insects are *Carpophilus hemipterus*.

11. The method of claim 8 wherein the insects are Lepidopteran species.

12. The method of claim 8 wherein the insects are *Helicoverpa zea*.

13. The method of claim 8 wherein the insects are *Spodoptera frugiperda*.

* * * * *